(12) United States Patent
Loibner et al.

(10) Patent No.: US 8,241,864 B2
(45) Date of Patent: Aug. 14, 2012

(54) METHOD FOR DETERMINING ACE2 ACTIVITY

(75) Inventors: Hans Loibner, Vienna (AT); Manfred Schuster, Schrick (AT); Evelyne Janzek-Hawlat, Vienna (AT)

(73) Assignee: Apeiron Biologics Forschungs-und Entwicklungsgesellschaft m.b.H., Vienna (AT)

( * ) Notice: Subject to any disclaimer, the term of this patent is extended or adjusted under 35 U.S.C. 154(b) by 109 days.

(21) Appl. No.: 12/445,906

(22) PCT Filed: Oct. 19, 2007

(86) PCT No.: PCT/AT2007/000488
§ 371 (c)(1),
(2), (4) Date: Jun. 17, 2010

(87) PCT Pub. No.: WO2008/046125
PCT Pub. Date: Apr. 24, 2008

(65) Prior Publication Data
US 2010/0261214 A1    Oct. 14, 2010

(30) Foreign Application Priority Data
Oct. 19, 2006    (AT) ................. A 1758/2006

(51) Int. Cl.
*C12Q 1/37*    (2006.01)
(52) U.S. Cl. .......................... 435/23; 435/7.4
(58) Field of Classification Search .......... 435/7.1, 435/7.4, 23
See application file for complete search history.

(56) References Cited

U.S. PATENT DOCUMENTS

| | | | |
|---|---|---|---|
| 4,946,778 A | 8/1990 | Ladner et al. | 435/69.6 |
| 5,591,591 A | 1/1997 | Bronstein et al. | 435/7.4 |
| 6,037,137 A | 3/2000 | Komoriya et al. | 435/23 |
| 6,194,556 B1* | 2/2001 | Acton et al. | 536/23.2 |
| 6,610,497 B1* | 8/2003 | Acton et al. | 435/7.1 |
| 2003/0124622 A1 | 7/2003 | Roemisch et al. | 435/7.4 |
| 2005/0287066 A1* | 12/2005 | Danilov et al. | 424/1.49 |
| 2007/0042452 A1* | 2/2007 | Lew et al. | 435/23 |
| 2011/0183366 A1* | 7/2011 | Batlle et al. | 435/24 |

FOREIGN PATENT DOCUMENTS

| | | |
|---|---|---|
| EP | 1 557 474 | 7/2005 |
| JP | 08 160046 | 6/1996 |
| WO | WO 90/00618 | 1/1990 |
| WO | WO 02/098448 | 12/2002 |

OTHER PUBLICATIONS

Burrell et al., "Myocardial infarction increases ACE2 expression in rat and humans," *Europ. Heart. J.*, 26:369-375, 2005.
Danilczyk and Penninger, "Angiotensin-converting enzyme II in the heart and the kidney,"*Circ. Res.*, 98:463-471, 2006.
Ferrario et al., "Novel angiotensin peptides regulate blood pressure, endothelial function, and natriuresis," *J. Am. Soc. Nephrol.*, 9:1716-1722, 1998.
Guy et al., "Angiotensin-converting enzyme-2 (ACE2): comparative modeling of the active site, specificity requirements, and chloride dependence," *Biochemistry*, 42:13185-13192, 2003.
Huang et al., "Novel peptide inhibitors of angiotensin-converting enzyme 2," *J. Biol. Chem.*, 278:15532-15540, 2003.
Imai et al., "Angiotensin-converting enzyme 2 protects from severe acute lung failure," *Nature*, 436:112-116, 2005.
Ishiyama et al., "Upregulation of angiotensin-converting enzyme 2 after myocardial infarction by blockade of angiotensin II receptors," *Hypertnesion*, 43:970-976, 2004.
Kuba et al., "Angiotensin-converting enzyme 2 in lung diseases," *Curr. Opin. Pharmacol.*, 6:271-276, 2006.
Towler et al., "ACE2 X-ray structures reveal a large hinge-bending motion important for inhibitor binding and catalysis," *J. Biol. Chem.*, 279:17996-18007, 2004.
Vickers et al., "Hydrolysis of biological peptides by human angiotensin-converting enzyme-related carboxypeptidase," *J. Biol. Chem.*, 277:14838-14843, 2002.
Ye et al., "Increased ACE 2 and decreased ACE protein in renal tubules from diabetic mice: a renoprotective combination?" *Hypertension*, 43:1120-1125, 2004.

* cited by examiner

*Primary Examiner* — Ralph Gitomer
(74) *Attorney, Agent, or Firm* — Fulbright & Jaworski L.L.P.

(57) ABSTRACT

Methods of determining ACE2 activity in a sample by reacting the sample with ACE2-binding units immobilized on a solid carrier and specific for a part of ACE2 not involved in the catalytic activity of ACE2. The reaction provides a signal that can be correlated with the ACE2 activity. These methods allow for ACE2 activity in complex solutions, such as bodily liquids or culture supernatants, to be quantitatively determined using the endogenous activity of the enzyme to be quantified by converting a signal-providing substrate.

26 Claims, 2 Drawing Sheets

Fig. 3

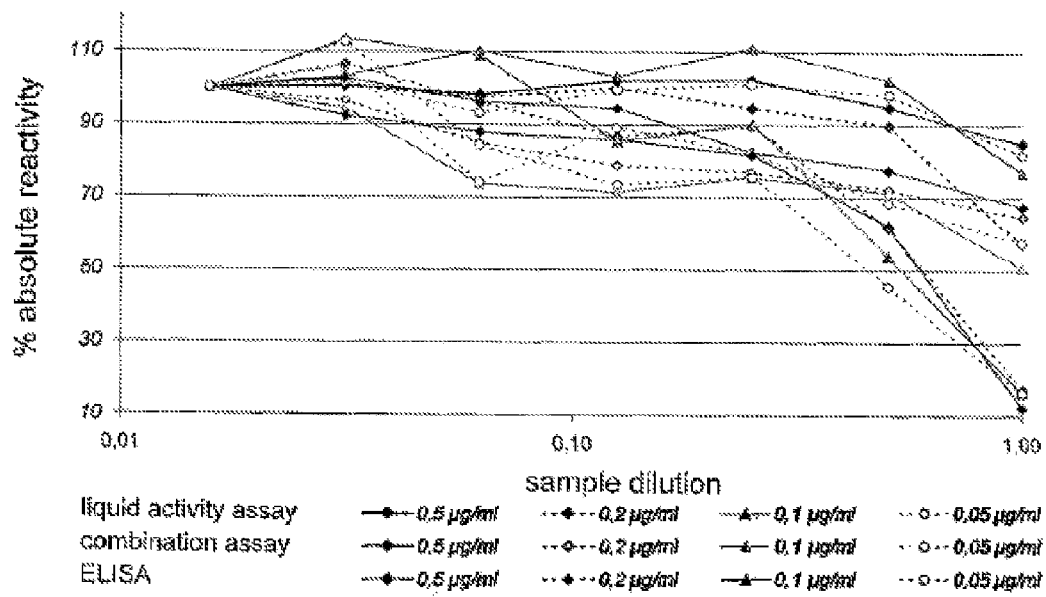

Fig. 4

MSSSSWLLLSLVAVTAAQSTIEEQAKTFLDKFNHEAEDLFYQSSLASWNYNTNITEE
NVQNMNNAGDKWSAFLKEQSTLAQMYPLQEIQNLTVKLQLQALQQNGSSVLSEDK
SKRLNTILNTMSTIYSTGKVCNPDNPQECLLLEPGLNEIMANSLDYNERLWAWESW
RSEVGKQLRPLYEEYVVLKNEMARANHYEDYGDYWRGDYEVNGVDGYDYSRGQL
IEDVEHTFEEIKPLYEHLHAYVRAKLMNAYPSYISPIGCLPAHLLGDMWGRFWTNLYS
LTVPFGQKPNIDVTDAMVDQAWDAQRIFKEAEKFFVSVGLPNMTQGFWENSMLTDP
GNVQKAVCHPTAWDLGKGDFRILMCTKVTMDDFLTAHHEMGHIQYDMAYAAQ
PFLLRNGANEGFHEAVGEIMSLSAATPKHLKSIGLLSPDFQEDNETEINFLLKQALTIV
GTLPFTYMLEKWRWMVFKGEIPKDQWMKKWWEMKREIVGVVEPVPHDETYCDPAS
LFHVSNDYSFIRYYTRTLYQFQFQEALCQAAKHEGPLHKCDISNSTEAGQKLFNMLRL
GKSEPWTLALENVVGAKNMNVRPLLNYFEPLFTWLKDQNKNSFVGWSTDWSPYAD
QSIKVRISLKSALGDKAYEWNDNEMYLFRSSVAYAMRQYFLKVKNQMILFGEEDVRV
ANLKPRISFNFFVTAPKNVSDIIPRTEVEKAIRMSRSRINDAFRLNDNSL**EFLGIQPTLG
PPNQPPVS**

METHOD FOR DETERMINING ACE2 ACTIVITY

This application is a national phase application under 35 U.S.C. §371 of International Application No. PCT/AT2007/000488 filed 19 Oct. 2007, which claims priority to Austrian Application No. 1758/2006 filed 19 Oct. 2006. The entire text of each of the above-referenced disclosures is specifically incorporated herein by reference without disclaimer.

The present invention relates to immunological determination of enzymatic enzyme activity.

Current methods of determining enzyme activities in quick screening methods are strongly influenced by interfering factors of diverse sources. Conventional assays for measuring enzyme activities provide for use of fluorescent or chromogenic compounds. For example, a fluorescent substrate is used for HIV-protease detection which has been modified with a fluorescent dansyl group at one end of the peptide, and with a fluorescence quencher at the other end of the peptide. The fluorescence signal measured is increased by cleavage of the peptide by the protease since the emitter part of the suppressing quencher will be separated. Fluorescent substrates for other enzymes may be modified by similar modifications of the substrate of the respective enzyme, as is disclosed in U.S. Pat. No. 6,037,137, EP 1 557 474 A, and WO 90/00618, e.g.

These assays, in particular in the field of high throughput, are susceptible to problems with the auto-fluorescence of biological components, partially due to the measured molecules themselves. Many of the compounds and natural extracts are themselves colored, or fluorescent, and are present in the solution during assay signal measurement. This results in that this interference restricts detection and sensitivity and/or the dynamic measurement region of the process. The interference can also be interpreted as enzyme inhibition, with the difficulty in inhibition assays of distinguishing the measured inhibition from the actual (bio)chemical inhibition of the enzyme.

U.S. Pat. No. 5,591,591 describes an assay for detecting proteases, wherein a dioxetane component with a proteolytic enzyme-specific amino acid, or a peptide, linked to a sample potentially containing the protease is added, with the amino acid being removed by the enzymatic reaction which, in turn, causes decomposition of the dioxetane, and chemiluminescence.

JP 8160046 relates to the use of a kit for determination of ACE activity.

WO 2002/098448 A1 relates to compounds which specifically bind ACE2 and modify the activity thereof.

US 2003/0124622 describes the measurement of the activity of a protease, wherein the protease is at first bound to an immobilized antibody, and a chromogenic substrate is added which changes its color by the influence of the enzyme activity. The change in the extinction can be correlated with the enzyme activity.

It is an object to develop quick measurement systems which are not influenced by contaminations, in particular systems for quick enzyme-activity measurement.

The present invention relates to a method of determing activity of ACE2, an enzyme of the reninangiotensin-aldosteron system, comprising the following steps:
  providing ACE2-binding units immobilized on a solid carrier and specific for a part of ACE2 which is not involved in the catalytic activity of ACE2;
  contacting the immobilized ACE2-binding units with a sample which potentially contains ACE2, wherein the ACE2 is bound by the ACE2-binding unit;
  removing non-binding portions of the sample from the enzyme bound to the ACE2-binding units;
  adding a substrate of ACE2 which is converted by the enzyme activity, with the conversion providing a signal; and
  measuring a change in the signal during a specific period of time, wherein the change can be correlated with the ACE2 activity.

The inventive method allows for the enzymatic activity in complex solutions, such as bodily liquids or culture supernatants, to be quantitatively determined by using the endogenous activity of the enzyme to be quantified by converting a signal-providing substrate.

For direct determination of active enzymes in complex solutions, such as bodily liquids, a method has been elaborated which combines two essential steps and enables a high sample throughput: the immunological binding of the enzyme to a carrier, e.g. a microtiter plate, thus achieving depletion of all the other components, followed by a specific enzymatic reaction based on a fluorescence-labeled substrate, which provides for a measurable signal.

In the first step, the complex solution is incubated, e.g. in a microtiter plate, in which, e.g., an ACE2-specific antibody has been immobilized beforehand. Such an antibody recognizes preferably a part of the enzyme which is not involved in the catalytic reaction, and the antibody does not affect the enzymatic reaction. If, to the contrary, the antibody recognizes regions of the enzyme which are directly involved in the enzymatic reactivity, the sensitivity of the assay will be reduced and/or the assay will not work any more since the enzyme activity has been blocked. All of the other components of the complex sample (e.g. serum) do not bind to the solid carrier, e.g. a plate surface, and will be removed from the system in a subsequent step, preferably washed off the plate. The washing steps can be optionally repeated, e.g. once, twice, three times or several times. Finally, only the properly bound enzyme remains on the plate. After addition of a fluorescence-labeled substrate, which will be cleaved by the enzyme and which has a much higher fluorescence in its cleaved state, the fluorescence will be measured after a defined period of incubation and compared to a standard of known activity and concentration. Usually, this is achieved by a two-component fluorescence-quenching system, with the fluorescence being increased by separation of the quencher.

Due to the influence of the enzyme on the substrate and/or due to the reaction by the enzyme, the same is changed preferably in extinction or fluorescence, which can be measured by optical methods. For example, from US 2003/0124622, chromogenic substrates are known which can be modified for the purpose of tracking a change in the extinction (or absorption). In further embodiments, the substrate has a fluorescent part and a fluorescence-quenching part, which can be separated by the enzyme activity. Thus, the reaction by the enzyme allows for a change in the fluorescence to be measured and tracked.

Preferably, the ACE2-binding unit is an antibody or an artificial, or natural, receptor of the enzyme which does not prevent ACE2-activity.

The inventively determined enzyme is ACE2, a peptidase, or protease, of the renin-angiotensin-aldosteron system (RAAS), which is also referred to as renin-angiotensin system (RAS). The proteolytic activity of RAS is a cascade of enzymatic steps for controlling blood pressure. In this context, ACE (angiotensin-converting enzyme) is probably the most well-known enzyme that converts angiotensin I to angiotensin II. Angiotensin II increases the blood pressure, which is why ACE inhibitors are often used for treating increased blood pressure. Directly after discovery of ACE2 it was assumed that it had the same activity as ACE (U.S. Pat. No. 6,194,556), which is why it was named after this enzyme. Both ACE and ACE2 are metalloproteases with a catalytic zinc-atom in the center. However, this original assumption was proven to be wrong. ACE and ACE2 are completely different in terms of activity as well as mechanistically. ACE increases blood pressure, whereas ACE2 decreases blood pressure (1). Mechanistically, ACE is a peptidyl dipeptidase, whereas ACE2 is a carboxy peptidase (9). Thus, ACE and ACE2 are two completely different enzymes with different prerequisites for measuring their activity.

ACE2 (angiotensin-converting enzyme 2) is a key enzyme of the renin-angiotensin system. As carboxy peptidase it is membrane-anchored (mACE2), as receptor it is expressed primarily on lung, kidney and heart cells, and cleaves diverse peptide substrates. Yet, in bodily fluids, ACE2 is also present as soluble protein (secreted ACE2, seACE2) without transmembrane domain and cytoplasmatic portion. Established substrate representatives are appelin, bradykinin and also angiotensin I, which is cleaved to angiotensin 1-9, or Ang-II, which is cleaved to Ang 1-7 (1, 2). ACE2 is to a great extent responsible for homeostasis of the organism (3).

Apeiron Biologics developed soluble ACE2 as a therapeutic agent for treating ARDS or ALI, two acute lung diseases, with a down-regulated ACE2 titer being one attendant symptom (4, 5) as several studies prove. Yet it is also provided for soluble ACE2 to be used for treating heart or kidney diseases (1, 6). Based on the fact that ACE2 plays an essential role in all these diseases, a robust determination method for quantification of soluble active ACE2 provides for crucial findings in the research of these indicators. Furthermore, such a method is also useful for determining pharmacokinetics and pharmacodynamics of a therapy employing soluble ACE2. Moreover, the content of enzymatically active ACE2 in bodily fluids is a key result which allows for access to diverse therapeutic and diagnostic fields.

Classical immunological determination methods (ELISA) of ACE2 concentrations only give an incomplete result since these methods are capable of detecting both active and enzymatically inactive enzyme. Yet, information on the function of ACE2 can be gathered by determination of the enzymatically-active portion only. So far the determination of peptidase activity in complex liquids, such as whole blood, serum or plasma samples, has proven to be difficult in the prior art since several components of these complex solutions can influence enzymatic reaction. Inhibiting components as well as peptidases of low specificity may falsify the measured substrate conversion in both directions, which usually prevents an approach to activity determination directly from these complex systems. This is why no satisfying system could so far be provided, in particular for ACE2, which also considers the complexity of the samples in which ACE2 can be measured.

Particularly preferably, ACE2 is selected from membrane-bound ACE2 (mACE2) and secreted ACE2 (seACE2), wherein the enzyme-binding unit is preferably specific for the C-terminal part of the extracellular domain of ACE2. Due to the vicinity of the hydrophobic region, ACE2 which is still kept in solution with the membrane domain by the aid of detergents should expose the C-terminal part in the hydrophilic solution to a significantly less degree. The sequence of ACE2 is indicated in FIG. 4 (SEQ ID No. 1), wherein the active center—zinc-binding motif HEXXH—is underlined. The inventive method works if the bound ACE2 still has enzyme activity. According to the sequence, the ACE2-binding unit is specific for a partial sequence of at least 4, preferably at least 5 or 6, particularly preferably at least 7, specifically preferably at least 8, consecutive amino acids of the 373 N-terminal amino acids of ACE2 or of the 362 C-terminal amino acids of ACE2. In particular embodiments, this partial sequence is selected from the 360, preferably 340 or 320 N-terminal, or C-terminal, amino acids. Such a sequence against which an ACE2-binding unit can be directed is EFL-GIQPTLGPPN (SEQ ID No. 2), e.g.

Furthermore, the crystal structure of ACE2 is published (9) and known as native enzyme (PDB database entry: 1R42), and as inhibitor-bound enzyme (PBD database entry: 1R4L). This native structure has a Zn atom as center point of the active center, and in the following serves as a reference for ACE2. A further crystal structure is known, e.g. under the PDB database entry 1O8A (native human ACE) in which a catalytic zinc atom is visible as well. Preferably, the enzyme-binding unit is specific for a part of at least 4, 5, 6, 7 or 8 amino acids of the enzyme, said part having a minimum distance from the active center of at least 0.5 nm, preferably 0.6 nm, particularly preferably 0.7 nm or 0.8 nm, particularly 0.9 nm or 1.0 nm (according to the crystal structure of the enzyme). To this end, the geometric center point of the partial sequence can be consulted, wherein the partial sequence does not necessarily have to consist of sequentially consecutive amino acids since, e.g., the antibodies do not recognize sequences but spatial structures. To detect the position of the active center, the mean value of the amino-acid coordinates or the position of the catalytic metal ion involved in the enzyme reaction can be consulted.

In specific embodiments, the parts, or partial sequences, of ACE2 may have up to 10, up to 12, up to 15, up to 20, up to 30, or even up to 40 or 50, amino acids of the enzyme.

An ACE2-binding unit preferably is an antibody which binds the C-terminal part of the extracellular domain of natural ACE2. Consequently, this leads to a directed presentation of the enzyme on the plate surface, in analogy to the presentation on the cell surface, without strongly influencing the ACE2 activity.

Activity-determination methods may be used for both fluorescent substrates and chromogenic substrates, with fluorescent substrates being preferred because of the sensitivity in case of blood samples.

In the inventive method, the ACE2-binding units are preferably selected from antibodies, antibody fragments, or antibody derivatives. Such units include Fv, Fab or F(ab)$_2$ portions of antibodies as well as single-chain antibodies (SCA), as disclosed in U.S. Pat. No. 4,946,778, or single-chain antigen-binding fragments (ScFv).

In specific embodiments, the antibodies, antibody fragments or antibody derivatives are polyclonal, wherein preferably antibodies, antibody fragments or antibody derivatives which preferably are specific for the active centers of the enzyme, are depleted to below 20%, preferably below 10%, more preferably below 5%, most preferably below 1%, e.g. by immunoabsorption, with parts of the active centers of the enzyme being presented in an immobilized fashion, the eluate containing the depleted preferred antibodies.

In other embodiments, the antibodies, antibody fragments or antibody derivatives are monoclonal. In this context, specific antibodies are selected which do not (or to a small extent) influence ACE2 activity. With particular enzymes, activity losses caused by the antibody binding cannot be avoided. Here, known selection methods (e.g. phage-display methods) however allow for this inhibition to be kept little. Accordingly, the enzymatic activity is inhibited by the antibody, the antibody fragment, or the antibody derivative, preferably by no more than 30%, preferably no more than 20%, particularly preferably no more than 10%, specifically preferably no more than 5%, most preferably no more than 1%. Particularly preferred antibodies can indeed even increase enzymatic activity.

The substrate which is used according to the invention preferably is a low-molecular peptide with a length of from 1 to 30 amino acids, preferably of from 1 to 20 amino acids, particularly preferably of from 1 to 10 amino acids, the peptide being cleavable by the enzyme, with the fluorescence part being covalently bound to one expected cleavage product, and with the quencher being covalently bound to a different expected cleavage product, preferably Mca-Ala-Pro-Lys (Dnp)-OH (Mca: (7-methoxy coumarin-4-yl)acetyl), provided that the enzyme is ACE2. Other peptide substrates are disclosed in (7) and (8), e.g. The coumarin-di-nitro-phenyl systems is particularly suited for ACE2. Other system are disclosed in U.S. Pat. No. 6,037,137, EP 1,557,474 A, and WO 90/00618.

The sample may include chromophoric and/or fluorescent contaminations. It is a substantial advantage of the inventive method that such interfering substances can be removed in the assay in a simple manner.

Preferably, the sample is selected from bodily fluids, homogenized fluid tissue samples, and cell-culture supernatants, preferably from whole blood, serum or plasma samples.

In a further aspect, the present invention provides for the use of the inventive method of in-vitro determination of ACE2 titers in whole blood, serum or plasma samples and/or of an enzyme in such a sample.

A further aspect relates to a method of diagnosing a disease symptom associated with abnormal ACE2 activity, characterized in that an animal or human sample is provided, and that the ACE2 activity is determined by an in-vitro method according to the present invention, with a change in the ACE2 activity, compared to the ACE2 activity in the healthy state, of more than 40% or 50%, preferably more than 60%, particularly preferably more than 75%, indicating a disease, or a risk of getting a disease. ACE2-indicated disease conditions can also be indicated via an ACE2-activity increase, e.g., myocardial infarction (10, 11), or via an ACE2-activity reduction, e.g. ARDS (4). In case of an ACE2-activity increase, the change in activity is preferably 100%, particularly at least 150%. The activity value in the healthy state strongly depends on the species and tissue, and can also be determined by the inventive method, e.g. as a mean value of healthy organisms, or in a reference tissue of the same organism which has not been affected by the disease. The inventive method thus allows for disease symptoms to be detected, and for a disease to be diagnosed, in a simple and reliable manner.

Diseases which are detected, or indicated, according to the invention are, e.g., cardiovascular diseases (in particular myocardial infarction), kidney diseases, and lung diseases, in particular ARDS or ALI. Specific ACE2-influenced lung diseases lead to liquid accumulation in the lung in which also the ACE2 activity can be determined. On that score, the bodily-fluid samples explicitly include a liquid in the lung and/or in the pulmonary alveoli.

In a further aspect, the present invention relates to a kit (suitable for conducting the inventive method) consisting of a solid carrier with immobilized enzyme-binding units, which are specific for a part of the enyzme not involved in the catalytic activity of the enyzme. As already described above, the enzyme is a protease, or peptidase, of RAS, preferably ACE2.

Preferably, the kit furthermore comprises a substrate of ACE2 which has a fluorescent part and a fluorescence-quenching part, which can be separated by ACE2 activity.

The immobilized ACE2 of the kit as well as the ACE2-binding units, and the substrate, can be provided for as described above.

The present invention will be explained in more detail by way of the following figures and examples, without being restricted thereto.

FIG. 1 shows an immunological determination of the enzymatic activity of ACE2 in complex solutions: after immunological enrichment of ACE2, solutions of different ACE2 concentrations (0 ng/ml: gray; 125 ng/ml: blue; 250 ng/ml: green; 500 ng/ml: yellow; and 1 µg/ml: red) were incubated with the peptide substrate Mca-Ala-Pro-Lys(Dnp)-OH for 17 hours. The fluorescence increase was measured at 320 nm/430 nm, and correlated with the enzyme amount present in the preparations.

FIG. 3 shows a comparison of the matrix-dependent signal intensity of the combination approach to ELISA, and activity assay in solution.

FIG. 4 shows a human ACE2 sequence (SEQ ID No. 1): the active center with the HEXXH-Zn-binding motif is underlined and bold, a C-terminal partial sequence (EFLGIQPTLGPPN; (SEQ ID No. 2)) as antibody epitope is highlighted in bold type.

EXAMPLE 1

Trial Conduct

Figure 1:
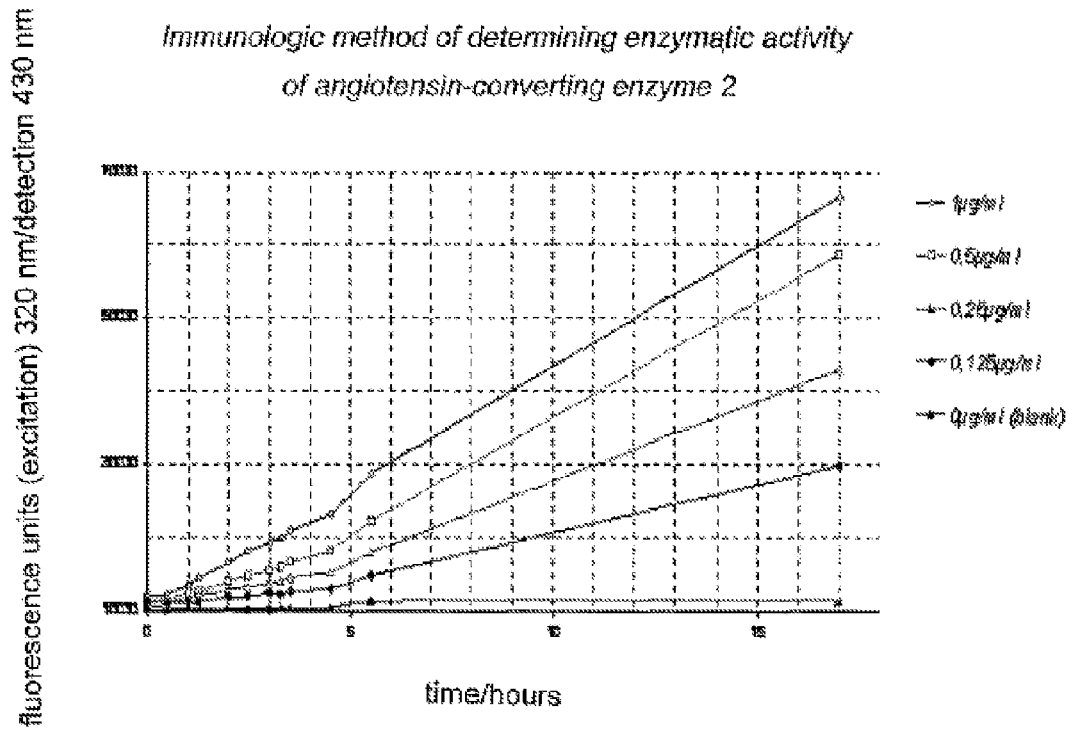

A murine polyclonal ACE2-specific antibody formulation was coated to a 96-well Maxisorp plate (Nunc), and subsequently incubated with four solutions of different ACE2 concentrations. After a washing step, the peptide substrate Mca-Ala-Pro-Lys(Dnp)-OH was added, and fluorescence was measured over a period of up to 17 hours at an excitement wave length of 320 nm, and at an emission wave length of 430 nm. FIG. 1 shows four standard curves of different ACE2 concentrations. Because of the underlying enzyme kinetics the product concentration (proportional to the fluorescence measured) appears in linear relationship to the enzyme amount present, provided that no limitation by the substrate occurs. Here, the slope of the straight line corresponds to the enzyme amounts present. In this context, the curves differ from each other the more significantly the longer the incubation period was after which the slope of the straight line remains constant in the region mentioned. Here, the likewise indicated Blank curve does not differ from the initial fluorescence increase and does not do so even after 17 hours of incubation. This is why the trial preparation can be incubated for different periods of time, as a function of desired sensitivity.

EXAMPLE 2

Absolute Measurement of an Enzyme Amount in Complex Matrix

The method presented shall allow for matrix-independent measurements of ACE2 activity. In this approach, the amount of active ACE2 was measured both by means of the combination assay described and by means of the "classical" activity assay in solution. A constant amount of ACE2 was added to serum samples which were collected at different points of time of a sepsis model. It is assumed that the concentration of substances which inhibit the ACE2 function increases as the ARDS symptoms are getting worse.

Figure 2:
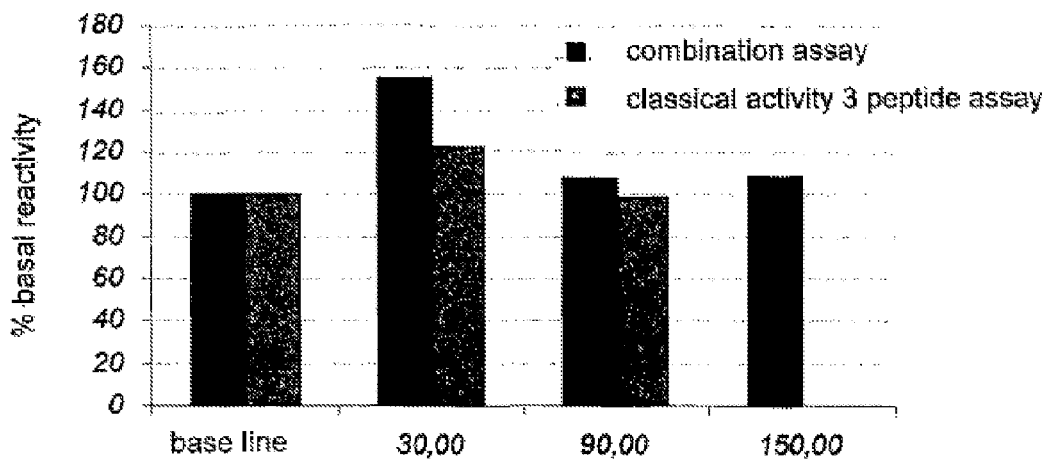
FIG. 2 shows an immunological determination of the enzymatic activity of ACE2 in complex solutions in the combination preparation: 0.2 µg/ml of ACE2 were added to serum samples of different points of time of an ARDS model, and measured by means of combination preparation (blue bars) and "classical" activity assay in solution (gray bars).

While the measurement values of both study methods almost correspond to the initial value (100%) during the first 90 minutes, ACE2 activity can be detected at the 150-min measurement point in the combination preparation only (FIG. 2). An explanation therefor is that the ACE2 inhibitors are removed from the system by means of a washing step in the combination assay only, and do not influence activity measurement. This observation makes said method suitable for analyzing active enzymes from complex solutions in a manner independent of the serum components.

EXAMPLE 3

Matrix Influences

The matrix-necessitated influence on the measurement-signal intensity (quenching) of the combination preparation was compared to that of an ELISA, and to that of an activity assay in solution. Constant ACE2 concentrations of 0.5 µg/ml, 0.2 µg/ml, 0.1 µg/ml, and 0.05 µg/ml, were measured in several serum dilutions, starting from 1 to 1:64. To compare the measurement methods indicated, the signal intensity was set from 1:64 to 100% in the highest sample dilution, and compared to the results of the other stages of dilution. This comparison parameter enables characterization of method-specific matrix-necessitated signal suppression (FIG. 3).

Here, the matrix influence on the ELISA method was the strongest: already at the two highest stages of dilution a signal suppression of 90% was measured which increased rapidly at higher serum concentration so that only a residual signal intensity of about 20% could be measured in the concentrated preparation. The activity preparation in solution showed the lowest matrix influence. In this context, one could recognize a significantly lower signal suppression to 70% in the concentrated sample. The combination approach shows similarities to each of the two different methods: it is characterized by a matrix dependency significantly stronger than in the case of activity approach. Yet, the signal intensity does not fall beyond 50% in the concentrated sample either.

Thus, this method allows for an ACE2-specific activity measurement even in concentrated serum samples: by the immunological ACE2-specific interaction of the first step, only this enzyme is introduced into the trial. In the second step, the measurement of its activity will not be falsified by other proteases, or ACE2 inhibitors, present in the matrix.

Literature

1. Danilczyk et al., Circ Res 98, 463-471 (2006).
2. Vickers et al., J Biol Chem 277, 14838-14843 (2002).
3. Ferrario et al., J Am Soc Nephrol 9, 1716-1722 (1998).
4. Imai et al., Nature 436, 112-116 (2005).
5. Kuba et al., Curr Opin Pharmacol (2006).
6. Ye et al., Hypertension 43, 1120-1125 (2004).
7. Huang et al., J Biol Chem 278, 15532-15540 (2003).
8. Guy et al., Biochemistry 42, 13185-13192 (2003).
9. Towler et al., J. Biol Chem 279, 17996-18007 (2004).
10. Burrell et al., Europ Heart J 26, 369-375 (2005).
11. Ishiyama et al., Hypertension 43, 970-976 (2004).

The invention claimed is:

1. A method of determining Angiotensin-converting Enzyme II (ACE2) activity, comprising:
providing ACE2-binding units immobilized on a solid carrier and specific only for a part of ACE2 which is not involved in the catalytic activity of ACE2;
contacting the immobilized ACE2-binding units with a sample which potentially contains ACE2, wherein the ACE2 is bound by the ACE2-binding unit;

removing non-binding portions of the sample from the ACE2 bound to the ACE2-binding units;

adding a substrate of ACE2 which is converted by the ACE2 activity, with the conversion providing a signal; and measuring a change in the signal during a specific period of time, wherein the change is correlated with the ACE2 activity.

2. The method of claim 1, wherein the signal is a change in extinction or fluorescence.

3. The method of claim 1, wherein the substrate has a fluorescent part and a fluorescence-quenching part, which can be separated by the ACE2 activity.

4. The method of claim 1, wherein the ACE2 is membrane-bound ACE2 (mACE2) or secreted ACE2 (seACE2).

5. The method of claim 1, wherein the ACE2-binding unit is specific for a partial sequence of at least 4 consecutive amino acids of the 373 N-terminal amino acids of ACE2 or of the 362 C-terminal amino acids of ACE2.

6. The method of claim 5, wherein the ACE2-binding unit is specific for a partial sequence of at least 6 consecutive amino acids of the 373 N-terminal amino acids of ACE2 or of the 362 C-terminal amino acids of ACE2.

7. The method of claim 6, wherein the ACE2-binding unit is specific for a partial sequence of at least 8 consecutive amino acids of the 373 N-terminal amino acids of ACE2 or of the 362 C-terminal amino acids of ACE2.

8. The method of claim 1, wherein the ACE2-binding unit is specific for a part of at least 4 amino acids of the ACE2 which have a minimum distance of 0.5 nm from the active center.

9. The method of claim 8, wherein the ACE2-binding unit is specific for a part of at least 6 amino acids of the ACE2 which have a minimum distance of 0.5 nm from the active center.

10. The method of claim 9, wherein the ACE2-binding unit is specific for a part of at least 8 amino acids of the ACE2 which have a minimum distance of 0.5 nm from the active center.

11. The method of claim 8, wherein the ACE2-binding unit is specific for a part of at least 4 amino acids of the ACE2 which have a minimum distance of 0.6 nm from the active center.

12. The method of claim 11, wherein the ACE2-binding unit is specific for a part of at least 4 amino acids of the ACE2 which have a minimum distance of 0.8 nm from the active center.

13. The method of claim 12, wherein the ACE2-binding unit is specific for a part of at least 4 amino acids of the ACE2 which have a minimum distance of 1.0 nm from the active center.

14. The method of claim 1, wherein the ACE2-binding units are antibodies, antibody fragments, and/or antibody derivatives.

15. The method of claim 14, wherein the antibodies, the antibody fragments, or the antibody derivatives, are polyclonal.

16. The method of claim 15, wherein the antibodies, antibody fragments, or antibody derivatives specific for the active centers of the ACE2 are depleted to below 20%.

17. The method of claim 16, wherein the antibodies, antibody fragments, or antibody derivatives specific for the active centers of the ACE2 are depleted to below 1%.

18. The method of claim 14, wherein the antibodies, the antibody fragments, or antibody derivatives are monoclonal.

19. The method of claim 1, wherein the substrate is a low-molecular peptide with a length of from 1 to 30 amino acid and the peptide is cleavable by ACE2, with the fluorescence part covalently bound to an expected cleavage product and the quencher is covalently bound to a different expected cleavage product.

20. The method of claim 19, wherein the quencher is covalently bound to Mca-Ala-Pro-Lys(Dnp)-OH.

21. The method of claim 19, wherein the substrate is a low-molecular peptide with a length of from 1 to 20 amino acid and the peptide is cleavable by ACE2.

22. The method of claim 21, wherein the substrate is a low-molecular peptide with a length of from 1 to 10 amino acid and the peptide is cleavable by ACE2.

23. The method of claim 1, wherein the sample contains chromophoric and/or fluorescent contaminations.

24. The method of claim 1, wherein the sample is a bodily fluid, homogenized fluid tissue sample, or cell-culture supernatant.

25. The method of claim 24, wherein the sample is whole blood, serum or a blood sample.

26. The method of claim 1, further defined as a method of in vitro determination of ACE2 titers in whole blood, serum, or plasma samples.

* * * * *

SEQUENCE LISTING

```
<160> NUMBER OF SEQ ID NOS: 2

<210> SEQ ID NO 1
<211> LENGTH: 740
<212> TYPE: PRT
<213> ORGANISM: Homo sapiens

<400> SEQUENCE: 1

Met Ser Ser Ser Ser Trp Leu Leu Leu Ser Leu Val Ala Val Thr Ala
1               5                   10                  15

Ala Gln Ser Thr Ile Glu Glu Gln Ala Lys Thr Phe Leu Asp Lys Phe
            20                  25                  30

Asn His Glu Ala Glu Asp Leu Phe Tyr Gln Ser Ser Leu Ala Ser Trp
        35                  40                  45

Asn Tyr Asn Thr Asn Ile Thr Glu Glu Asn Val Gln Asn Met Asn Asn
    50                  55                  60

Ala Gly Asp Lys Trp Ser Ala Phe Leu Lys Glu Gln Ser Thr Leu Ala
65                  70                  75                  80

Gln Met Tyr Pro Leu Gln Glu Ile Gln Asn Leu Thr Val Lys Leu Gln
                85                  90                  95

Leu Gln Ala Leu Gln Gln Asn Gly Ser Ser Val Leu Ser Glu Asp Lys
            100                 105                 110

Ser Lys Arg Leu Asn Thr Ile Leu Asn Thr Met Ser Thr Ile Tyr Ser
        115                 120                 125

Thr Gly Lys Val Cys Asn Pro Asp Asn Pro Gln Glu Cys Leu Leu Leu
    130                 135                 140

Glu Pro Gly Leu Asn Glu Ile Met Ala Asn Ser Leu Asp Tyr Asn Glu
```

```
            145                 150                 155                 160
Arg Leu Trp Ala Trp Glu Ser Trp Arg Ser Glu Val Gly Lys Gln Leu
                165                 170                 175
Arg Pro Leu Tyr Glu Glu Tyr Val Val Leu Lys Asn Glu Met Ala Arg
                180                 185                 190
Ala Asn His Tyr Glu Asp Tyr Gly Asp Tyr Trp Arg Gly Asp Tyr Glu
                195                 200                 205
Val Asn Gly Val Asp Gly Tyr Asp Tyr Ser Arg Gly Gln Leu Ile Glu
                210                 215                 220
Asp Val Glu His Thr Phe Glu Glu Ile Lys Pro Leu Tyr Glu His Leu
225                 230                 235                 240
His Ala Tyr Val Arg Ala Lys Leu Met Asn Ala Tyr Pro Ser Tyr Ile
                245                 250                 255
Ser Pro Ile Gly Cys Leu Pro Ala His Leu Leu Gly Asp Met Trp Gly
                260                 265                 270
Arg Phe Trp Thr Asn Leu Tyr Ser Leu Thr Val Pro Phe Gly Gln Lys
                275                 280                 285
Pro Asn Ile Asp Val Thr Asp Ala Met Val Asp Gln Ala Trp Asp Ala
                290                 295                 300
Gln Arg Ile Phe Lys Glu Ala Glu Lys Phe Phe Val Ser Val Gly Leu
305                 310                 315                 320
Pro Asn Met Thr Gln Gly Phe Trp Glu Asn Ser Met Leu Thr Asp Pro
                325                 330                 335
Gly Asn Val Gln Lys Ala Val Cys His Pro Thr Ala Trp Asp Leu Gly
                340                 345                 350
Lys Gly Asp Phe Arg Ile Leu Met Cys Thr Lys Val Thr Met Asp Asp
                355                 360                 365
Phe Leu Thr Ala His His Glu Met Gly His Ile Gln Tyr Asp Met Ala
370                 375                 380
Tyr Ala Ala Gln Pro Phe Leu Leu Arg Asn Gly Ala Asn Glu Gly Phe
385                 390                 395                 400
His Glu Ala Val Gly Glu Ile Met Ser Leu Ser Ala Ala Thr Pro Lys
                405                 410                 415
His Leu Lys Ser Ile Gly Leu Leu Ser Pro Asp Phe Gln Glu Asp Asn
                420                 425                 430
Glu Thr Glu Ile Asn Phe Leu Leu Lys Gln Ala Leu Thr Ile Val Gly
                435                 440                 445
Thr Leu Pro Phe Thr Tyr Met Leu Glu Lys Trp Arg Trp Met Val Phe
                450                 455                 460
Lys Gly Glu Ile Pro Lys Asp Gln Trp Met Lys Lys Trp Trp Glu Met
465                 470                 475                 480
Lys Arg Glu Ile Val Gly Val Val Glu Pro Val Pro His Asp Glu Thr
                485                 490                 495
Tyr Cys Asp Pro Ala Ser Leu Phe His Val Ser Asn Asp Tyr Ser Phe
                500                 505                 510
Ile Arg Tyr Tyr Thr Arg Thr Leu Tyr Gln Phe Gln Phe Gln Glu Ala
                515                 520                 525
Leu Cys Gln Ala Ala Lys His Glu Gly Pro Leu His Lys Cys Asp Ile
                530                 535                 540
Ser Asn Ser Thr Glu Ala Gly Gln Lys Leu Phe Asn Met Leu Arg Leu
545                 550                 555                 560
Gly Lys Ser Glu Pro Trp Thr Leu Ala Leu Glu Asn Val Val Gly Ala
                565                 570                 575
```

-continued

```
Lys Asn Met Asn Val Arg Pro Leu Leu Asn Tyr Phe Glu Pro Leu Phe
            580                 585                 590

Thr Trp Leu Lys Asp Gln Asn Lys Asn Ser Phe Val Gly Trp Ser Thr
        595                 600                 605

Asp Trp Ser Pro Tyr Ala Asp Gln Ser Ile Lys Val Arg Ile Ser Leu
    610                 615                 620

Lys Ser Ala Leu Gly Asp Lys Ala Tyr Glu Trp Asn Asp Asn Glu Met
625                 630                 635                 640

Tyr Leu Phe Arg Ser Ser Val Ala Tyr Ala Met Arg Gln Tyr Phe Leu
                645                 650                 655

Lys Val Lys Asn Gln Met Ile Leu Phe Gly Glu Glu Asp Val Arg Val
            660                 665                 670

Ala Asn Leu Lys Pro Arg Ile Ser Phe Asn Phe Phe Val Thr Ala Pro
        675                 680                 685

Lys Asn Val Ser Asp Ile Ile Pro Arg Thr Glu Val Glu Lys Ala Ile
    690                 695                 700

Arg Met Ser Arg Ser Arg Ile Asn Asp Ala Phe Arg Leu Asn Asp Asn
705                 710                 715                 720

Ser Leu Glu Phe Leu Gly Ile Gln Pro Thr Leu Gly Pro Pro Asn Gln
                725                 730                 735

Pro Pro Val Ser
            740

<210> SEQ ID NO 2
<211> LENGTH: 13
<212> TYPE: PRT
<213> ORGANISM: Homo sapiens

<400> SEQUENCE: 2

Glu Phe Leu Gly Ile Gln Pro Thr Leu Gly Pro Pro Asn
1               5                   10
```